United States Patent
Brown et al.

[11] Patent Number: 5,736,085
[45] Date of Patent: Apr. 7, 1998

[54] CATHETER BEVELING AND DIE CUT PROCESS

[75] Inventors: Ronald C. Brown, Santa Cruz, Calif.; Joseph J. Chang, Avon; Dennis Bialecki, Oxford, both of Conn.

[73] Assignee: Johnson & Johnson Medical, Inc., Arlington, Tex.

[21] Appl. No.: 773,938

[22] Filed: Dec. 30, 1996

[51] Int. Cl.⁶ .............................. B29C 37/02; B28B 7/14
[52] U.S. Cl. .......... 264/161; 264/163; 264/296; 264/320; 264/322; 264/DIG. 66; 425/292; 425/393; 425/806
[58] Field of Search ........................ 264/161, 163, 264/320, 296, DIG. 66, 322, 150; 425/393, 292, 298, 302.1, 806

[56] References Cited

U.S. PATENT DOCUMENTS

| | | | |
|---|---|---|---|
| 3,843,300 | 10/1974 | McFarlane | 425/384 |
| 3,929,959 | 12/1975 | Findlay et al. | 264/292 |
| 3,929,960 | 12/1975 | Findlay et al. | 264/292 |
| 3,983,203 | 9/1976 | Corbett | 264/296 |
| 4,177,237 | 12/1979 | Uneo et al. | 264/296 |
| 4,264,294 | 4/1981 | Ruiz | 425/466 |
| 4,292,270 | 9/1981 | Hannah et al. | 264/296 |
| 4,373,894 | 2/1983 | Peppel | 264/296 |
| 4,404,159 | 9/1983 | McFarlane | 264/296 |
| 4,551,292 | 11/1985 | Fletcher et al. | 264/322 |
| 4,961,809 | 10/1990 | Martin | 264/322 |
| 5,102,324 | 4/1992 | Bullard et al. | 425/135 |
| 5,209,882 | 5/1993 | Hattori et al. | 264/296 |
| 5,397,512 | 3/1995 | Sloane, Jr. et al. | 264/25 |
| 5,409,644 | 4/1995 | Martin et al. | 264/296 |
| 5,425,903 | 6/1995 | Sloane, Jr. et al. | 264/22 |

Primary Examiner—Jan H. Silbaugh
Assistant Examiner—Mark Eashoo
Attorney, Agent, or Firm—Joseph F. Shirtz

[57] ABSTRACT

A process for forming the tips on catheters is described in which the catheter is placed on a mandrel and molded in a mold. The mandrel may then be removed and a second mandrel inserted. The second mandrel having a larger diameter and adapted to contact inner surface of the mold to thereby cut any flash formed at the end of the catheter and separate the flash from the catheter tip. Alternatively, the mandrel and catheter are inserted into the mold to mold the outer surface of the catheter thereafter removed and inserted into a die to punch the flash from the tip of the catheter material. The punch process may be carried out by either the same mandrel or a second mandrel adapted to the purpose of cutting or punching the flash from the catheter.

10 Claims, 3 Drawing Sheets

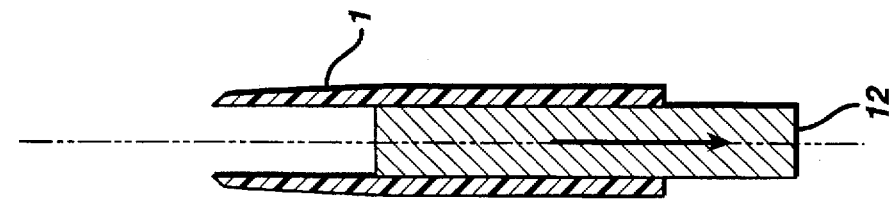
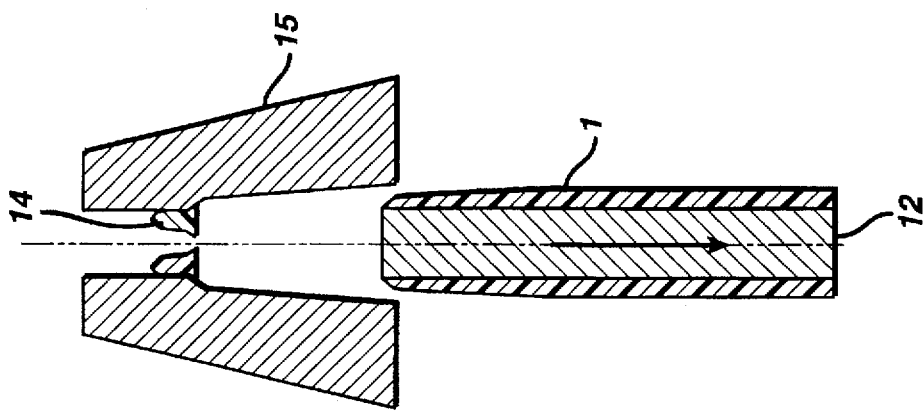
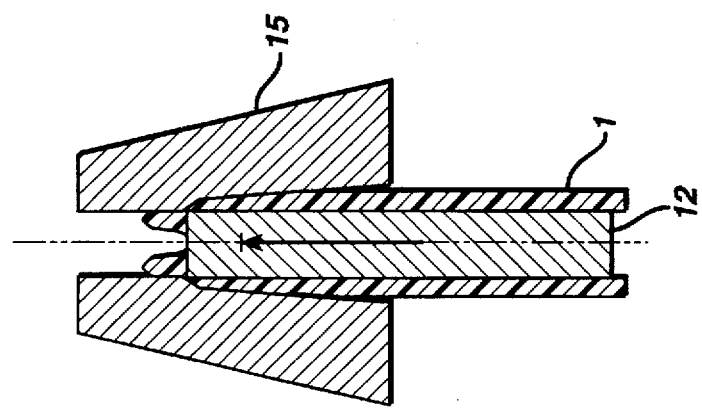
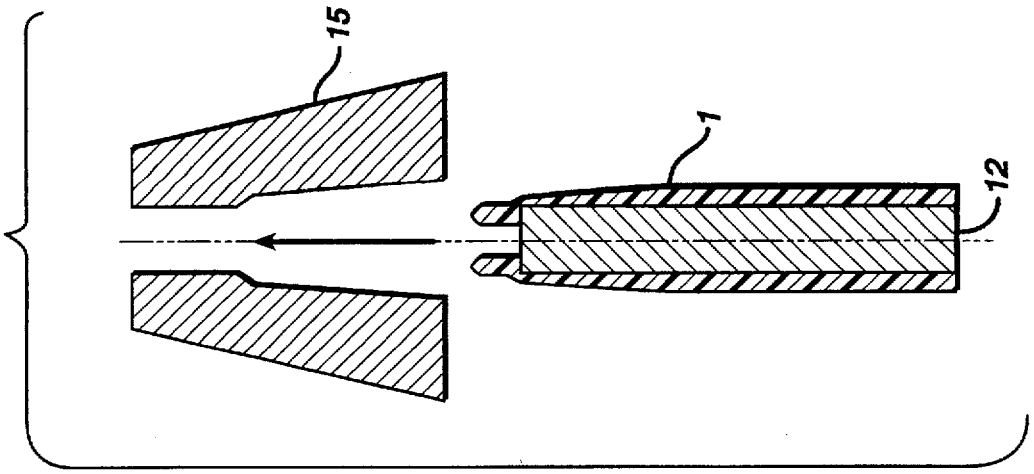

CATHETER BEVELING AND DIE CUT PROCESS

FIELD OF THE INVENTION

The present invention relates to processes for forming medical devices and in particular for forming beveled tips on tubular catheter products.

BACKGROUND OF THE INVENTION

It has long been known to taper the tip of a catheter, in particular, a peripherally inserted intravenous catheter in order to ease the insertion process. It has further been found and most products today have a dual bevel formed at the catheter tip. The first bevel is a taper of 3° and the second bevel is a taper of approximately 27°. These tips may be formed for example by laser cutting as shown in U.S. Pat. No. 5,425,903 or by molding as shown in U.S. Pat. No. 4,661,300 to Daugherty.

The Daugherty patent shows a molding process in which a single step operation is used to form and clip the catheter. That is, the catheter is placed on a mandrel extending with the catheter material extending beyond the mandrel and this assembly is then inserted into a heated mold to form the outer surface of the catheter. The mandrel is advanced to a point where it engages the mold surface to clip the flash from the catheter in a single step.

The single step process, however, has significant disadvantages in that it provides for short tool life in that both the mold and the mandrel are used also as cutting devices and therefore must engage and wear upon each other. This means that during usage the outer surface formed on the catheter varies as the contact between the mandrel and the die wears upon the inner surface of the die. Furthermore, tooling must be replaced in order to maintain a sharp interface edge between the mandrel and mold to provide appropriate cutting action.

SUMMARY OF THE INVENTION

The invention relates to a process for beveling the tip of an intravenous catheter. The process includes the steps of placing a tubular catheter on a mandrel which will carry the catheter during at least a portion of the processing. The mandrel extends beyond the end of the tubular catheter material in at least one embodiment. A mold is provided and is heated to a sufficient temperature to soften the tubular catheter material. The mold is provided with a tapered inner mold surface.

The catheter is inserted into the mold by inserting the mandrel-carrying catheter therein. The mandrel may pass entirely through the mold and extend out an opposite end thereof.

Insertion of the catheter-carrying mandrel into the mold allows the catheter material to melt and flow by contact of the material with the inner surface of the mold. This forms a predetermined outer surface to the catheter and a portion of flash extending from the tip of the catheter. The mandrel is then removed from the mold and a second mandrel or cutter is inserted into the catheter while still in the mold. This mandrel or cutter has a larger diameter then the first mandrel and by advancing the second mandrel until it contacts a portion of the mold, the tip of the catheter is trimmed of its flash.

In an alternate embodiment of the present invention, the tubular catheter is placed over a mandrel and a heated mold is provided as described above. The catheter and mandrel are inserted into the mold and the catheter material is allowed to melt and flow along the inner surface of the mold. The catheter material extends beyond the desired catheter tip forming a portion of flash. The catheter with flash is removed from the mold and thereafter inserted into a die. The flash is severed from the tip of the catheter material by inserting the mandrel into the die until the mandrel contacts an inner surface of the die.

In this process, the mandrel used in the die-cutting operation may be different from that used in the molding operation, thus limiting the wear on the mandel use in the molding operation. Alternatively, the same mandrel may be used in both the molding and die-cutting operation. It is also contemplated that in the molding step, the mandrel may pass completely through the mold and out an opening at a second end of the mold while still permitting flash to extend beyond the end of the desired catheter tip.

BRIEF DESCRIPTION OF THE DRAWINGS

The invention will now be described with reference to the attached drawings wherein:

FIG. 6 shows insertion of the molded catheter and mandrel into a die at a second station in the process of FIG. 3;

FIG. 7 shows the cutting of the flash from the end of the formed catheter in the process of FIG. 3;

FIG. 8 shows withdrawal of the catheter and mandrel from the die in the process of FIG. 3; and, FIG. 9 shows withdrawal of the mandrel from the catheter after formation of the catheter tip.

DETAILED DESCRIPTION OF THE PREFERRED EMBODIMENT

Catheters may be formed of different materials and are normally extruded polymer tubes. The most prevalent materials used in catheters today are polytetrafluoroethylene and polyurethane.

The process will be described generically, however, the particular process parameters may easily be determined by one of ordinary skill in the art. For example, the temperature of the mold is selected in order to provide for an appropriate molding characteristic without crushing of the catheter material (due to under heating) or excessive running of the catheter material (due to over heating).

Figure 2:
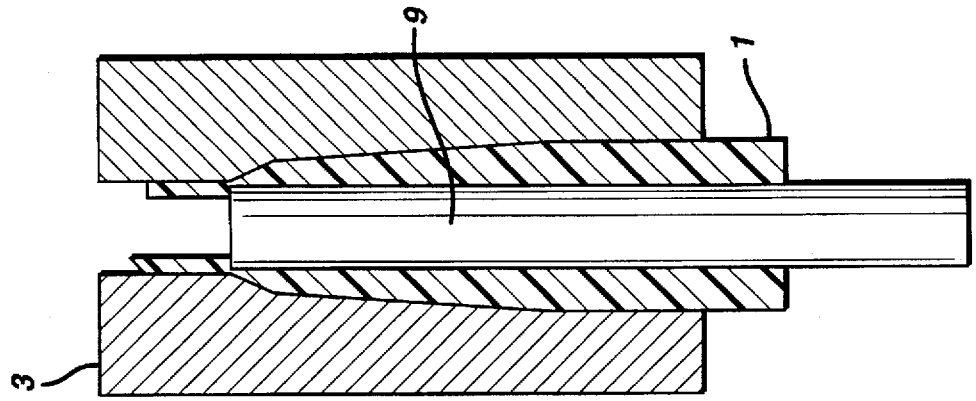
FIG. 2 depicts the cutting step of the process of FIG. 1.
Figure 1:
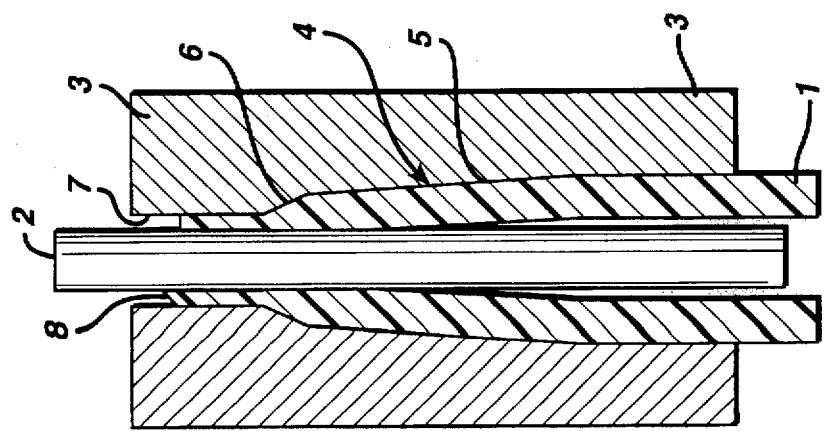
FIG. 1 depicts the molding process of a first embodiment of the invention.
Figure 5:
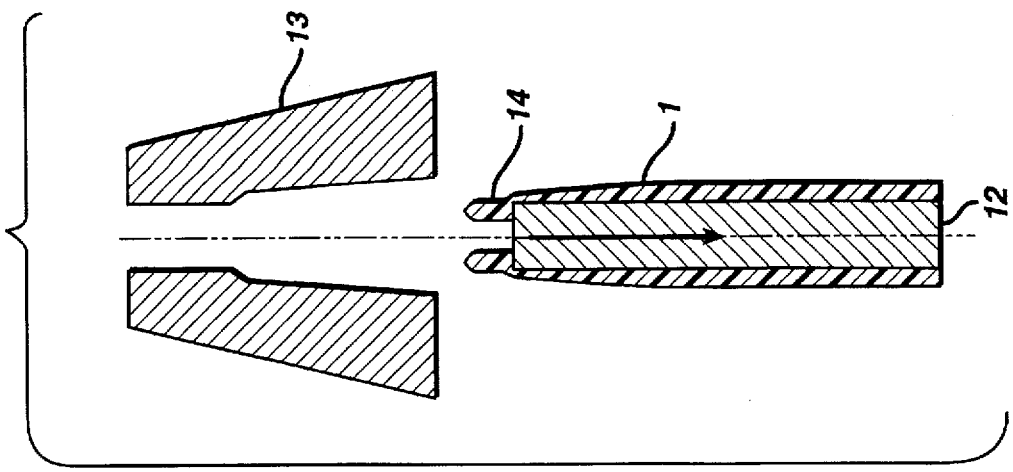
FIG. 5 shows withdrawal of the catheter and mandrel from the mold depicted in FIG. 3.

A first embodiment of the process of the present application is depicted in FIGS. 1 and 2. In this process a tubular catheter 1, for example a polytetrafluoroethylene (PTFE) catheter, is placed over a carrying mandrel 2 of a given diameter (for example 20 ga. 0.045"OD). The mandrel 2 is made of stainless steel and may be moved in any known manner such as by pneumatic actuators, stopper motors or the like. A mold 3 is provided having a tapered inner surface which compliments the final shape desired on the outer surface of the catheter. The mold is formed or machined from steel and has an opening passing completely through the interior. The opening has two tapers a first taper 5 of 3° extending along the distal portion of the tube and a second taper 6 of 27° at the tip.

In the process the mold 3 is heated to approximately 680° F. and the catheter 1 and mandrel 2 are inserted into the mold 3. The contact between the catheter material and the mold 3 heats the catheter material to approximately its melting point and permits it to begin flowing within the mold 3 and partially out the opening 7 at a second end of the mold. The mandrel 2 is of a diameter which permits passage completely through the mold without contacting the mold surface. An area of flash 8 is formed at the end of the catheter which will later be severed from the catheter tip.

The first mandrel is withdrawn from the mold 3 leaving the catheter material within the mold. A second mandrel 9 or punch is then inserted into the catheter 1. The second mandrel 9 has a diameter larger than the first mandrel 2 and may be for example 0.037" for an 18 ga. IVC in diameter. This mandrel 9 is sized such that it will not pass through the opening at the second end of the mold but rather will engage the inner surface of the mold 3 to punch and cut the flash 8 from the tip of the catheter. The second mandrel 9 is then inserted through the catheter 1 until such point where it does engage the inner mold surface, thus cutting the flash material from the end of the catheter. After this process the mandrel and catheter are withdrawn from the mold and the mold 3 is reheated for a second operation. The catheter then continues along with its processing to be formed into a final catheter product.

A second embodiment of the invention is depicted in FIGS. 3 through 9. This embodiment may best be described as a two station process.

Figure 4:
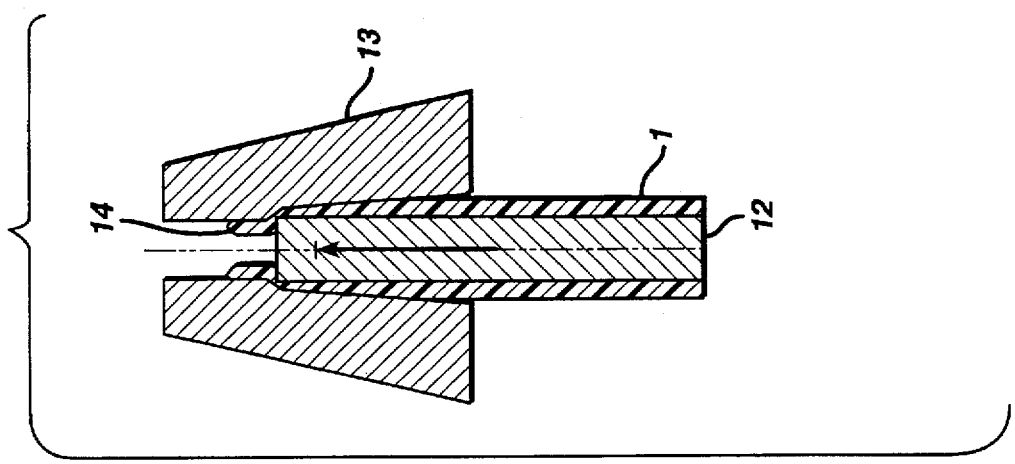
FIG. 4 shows a molding process in the second embodiment of the invention depicted in FIG. 3.
Figure 3:
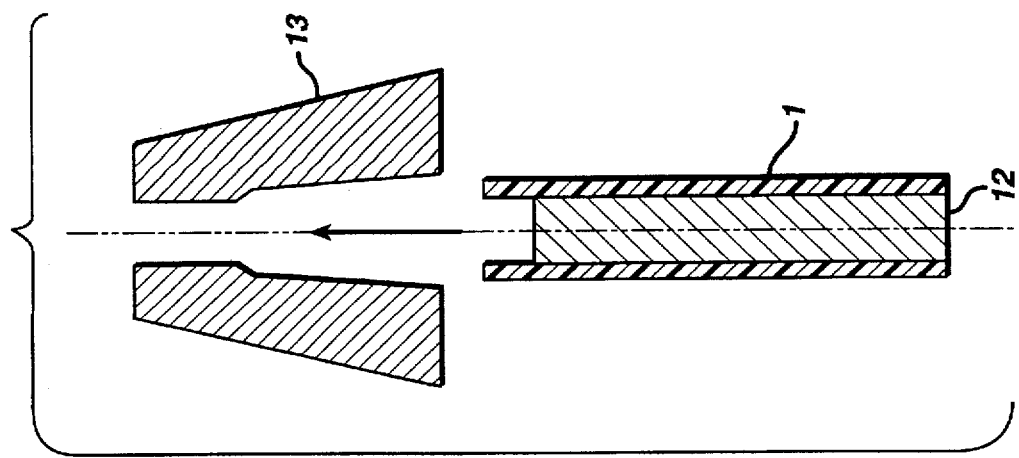
FIG. 3 shows the insertion of a catheter carrying mandrel into a mold in a second embodiment of the invention.

In the second embodiment a catheter 1 is placed upon a mandrel 12 for insertion into a mold 13 in a manner similar to that provided for the first embodiment. The catheter 1 is positioned on the mandrel 12 with a portion of the catheter material extending beyond the mandrel. This mandrel 12 and catheter 1 assembly is then inserted into the heated mold 13. This mold 13 is similar to the mold described in connection with the first embodiment and is also heated to a temperature of 680° F. As seen in FIG. 4 the mandrel 12 is inserted to a point where it does not contact the inner mold surface but the catheter material is permitted to heat and conform to the inner mold surface with a portion of flash 14 extending beyond the desired end of the catheter. The molded catheter and mandrel 12 are then withdrawn from the mold and cooled. It may be preferable to permit the mold to cool or withdraw the catheter material when partially cooled and permit it to finally cool outside of the mold.

As shown in FIG. 6 the molded catheter is then inserted into a die 15 at a second station. This may be for example a second station on a turn table wherein the same mandrel 12 carrying the catheter 1 is moved from the mold position to a position aligned with the die 15. The mandrel and molded catheter are then inserted into the die 15 to such a point that the mandrel engages the die surface to cut the flash from the end of the catheter.

After the flash has been cut from the catheter the final formed catheter and mandrel are removed from the die and the catheter is removed from the mandrel. In this way the important molding surface of the first station does not contact the mandrel and therefore is not subject to the wear created in prior art processes where the mandrel and mold engaged one another.

Furthermore the die may be made out of material selected for its hardness and without regard for heat conductivity. In this way the mold can be optimized for its heat mass/ conductivity and the die can be optimized for its hardness and ability to withstand the wear caused by contact with the mandrel.

The invention has been described in connection with certain preferred embodiments. The embodiments may be modified and changed without departing from the scope of the invention which is claimed with reference to the claims attached hereto. For example, a tubular sharpened blade may be substituted for the mandrel in the cutting opertion, or the die may have a blade substitution therefor.

We claim:

1. A process for beveling a tip of an intravenous catheter comprising the steps of:
   a) placing a tubular catheter over a first mandrel with said first mandrel extending beyond the tip of the catheter to be beveled;
   b) heating a mold having a tapered inner mold surface;
   c) inserting the catheter carrying first mandrel into said mold to engage the material of the catheter with said tapered inner mold surface;
   d) allowing the material to melt and flow on said tapered inner mold surface to form a predetermined beveled outer surface of the catheter tip with flash extending beyond the beveled catheter tip;
   e) removing said first mandrel from the catheter in said mold;
   f) inserting a second mandrel of a larger diameter into the catheter in said mold; and
   g) advancing said second mandrel until a portion of said second mandrel engages said mold to cut the flash from the beveled catheter tip.

2. The process according to claim 1 wherein said first mandrel has a diameter from 0.0330" to 0.0340" and said second mandrel has a diameter from 0.0365" to 0.0375" for 18 ga. IVC.

3. The process according to claim 1 wherein the tubular catheter is formed of polytetrafluoroethylene and said mold is heated to a range from about 650° F. to about 750° F.

4. The process according to claim 1 wherein said mold has an open second end and said first mandrel is sized to pass completely through said mold and out of said open second end upon insertion within the mold.

5. The process for beveling a tip of an I.V. catheter comprising:
   a) placing a tubular catheter over a mandrel;
   b) heating a mold having a tapered inner mold surface;
   c) inserting the catheter and said mandrel into said mold to engage the catheter with said tapered inner mold surface;
   d) allowing the material of the catheter to melt on said tapered inner mold surface to form a predetermined beveled outer surface on the catheter tip with flash extending beyond the beveled catheter tip;
   e) removing the catheter and said mandrel from said mold; and
   f) inserting the catheter into a die and severing said flash from the beveled catheter tip by contacting a mandrel with an inner surface of said die.

6. The process of according to claim 5 wherein the mandrel used to contact said inner surface of said die is a mandrel different from the mandrel on which the tubular catheter is placed for heating and molding.

7. The process according to claim 5 wherein the mandrel which contacts said inner surface of said die is the same mandrel inserted into said mold to engage the catheter with said inner mold surface in order to mold the catheter.

8. The process according to claim 5 wherein the first inserting step includes passing said mandrel completely through said mold and out a second opening of said mold.

9. The process according to claim 5 wherein said tubular catheter is formed of polytetrafluoroethylene.

10. The process according to claim 5 wherein the heating step includes heating said mold to a temperature from about 650° F., to about 750° F.

* * * * *